US011219774B2

(12) United States Patent
Bornzin et al.

(10) Patent No.: US 11,219,774 B2
(45) Date of Patent: Jan. 11, 2022

(54) VENTRICULAR LEADLESS IMPLANTABLE MEDICAL DEVICE WITH DUAL CHAMBER SENSING AND METHOD FOR SAME

(71) Applicant: Pacesetter, Inc., Sylmar, CA (US)

(72) Inventors: Gene A. Bornzin, Santa Monica, CA (US); Nima Badie, Berkeley, CA (US); Chunlan Jiang, Northridge, CA (US); David Ligon, Truckee, CA (US)

(73) Assignee: Pacesetter, Inc., Sylmar, CA (US)

( * ) Notice: Subject to any disclaimer, the term of this patent is extended or adjusted under 35 U.S.C. 154(b) by 174 days.

(21) Appl. No.: 16/425,775

(22) Filed: May 29, 2019

(65) Prior Publication Data

US 2020/0376282 A1    Dec. 3, 2020

(51) Int. Cl.
| | | |
|---|---|---|
| *A61N 1/375* | (2006.01) | |
| *A61N 1/365* | (2006.01) | |
| *A61N 1/368* | (2006.01) | |
| *A61N 1/05* | (2006.01) | |
| *A61N 1/362* | (2006.01) | |
| *A61N 1/39* | (2006.01) | |
| *A61B 5/352* | (2021.01) | |
| *A61B 5/361* | (2021.01) | |

(Continued)

(52) U.S. Cl.
CPC ......... *A61N 1/3756* (2013.01); *A61N 1/3682* (2013.01); *A61N 1/36592* (2013.01); *A61N 1/3962* (2013.01); *A61B 5/352* (2021.01); *A61B 5/361* (2021.01); *A61B 5/364* (2021.01); *A61B 5/366* (2021.01); *A61N 1/056* (2013.01); *A61N 1/3622* (2013.01); *A61N 1/36542* (2013.01)

(58) Field of Classification Search
CPC .............. A61N 1/3756; A61N 1/36592; A61N 1/3962; A61N 1/3682; A61N 1/36542; A61N 1/056; A61N 1/3622; A61B 5/046; A61B 5/0456; A61B 5/0472; A61B 5/0468
See application file for complete search history.

(56) References Cited

U.S. PATENT DOCUMENTS 3,946,744 A   3/1976 Auerbach
5,713,367 A   2/1998 Arnold et al.
(Continued)

OTHER PUBLICATIONS

Extended European Search Report for corresponding EP Application No. 19172674.4 dated Oct. 4, 2019 (8 pages).
(Continued)

*Primary Examiner* — Gary Jackson
*Assistant Examiner* — Alexander M Eisenberg
(74) *Attorney, Agent, or Firm* — The Small Patent Law Group LLC; Dean D. Small

(57) ABSTRACT

A computer implemented method and device for providing dual chamber sensing with a single chamber leadless implantable medical device (LIMD) are provided. The method is under control of one or more processors in the LIMD configured with specific executable instructions. The method obtains a far field (FF) cardiac activity (CA) signals for activity in a remote chamber of a heart and compares the far field CA signals to a P-wave template to identify an event of interest associated with the remote chamber. The method sets an atrial-ventricular (AV) delay based on the P-wave identified and delivers pacing pulses at a pacing site of interest to a local chamber based on the AV delay.

18 Claims, 7 Drawing Sheets

(51) Int. Cl.
*A61B 5/364* (2021.01)
*A61B 5/366* (2021.01)

(56) References Cited

U.S. PATENT DOCUMENTS

| | | | |
|---|---|---|---|
| 6,912,418 B1* | 6/2005 | Florio | A61B 5/04525 |
| | | | 607/9 |
| 7,248,921 B2 | 7/2007 | Palreddy et al. | |
| 7,294,108 B1 | 11/2007 | Bornzin et al. | |
| 7,706,865 B1* | 4/2010 | Snell | A61B 5/7203 |
| | | | 600/509 |
| 7,894,894 B2 | 2/2011 | Stadler et al. | |
| 8,135,456 B2 | 3/2012 | Haluska | |
| 8,260,404 B1 | 9/2012 | Bharmi et al. | |
| 8,332,022 B2 | 12/2012 | Brown et al. | |
| 8,391,980 B2 | 3/2013 | Bornzin et al. | |
| 8,831,713 B2 | 9/2014 | Stadler et al. | |
| 8,831,747 B1 | 9/2014 | Min et al. | |
| 9,044,610 B2 | 6/2015 | Rosenberg et al. | |
| 9,168,380 B1* | 10/2015 | Greenhut | A61N 1/37211 |
| 9,174,062 B2 | 11/2015 | Stadler et al. | |
| 9,216,285 B1 | 12/2015 | Boling et al. | |
| 9,232,485 B2 | 1/2016 | Wu et al. | |
| 9,333,351 B2 | 5/2016 | Arnold et al. | |
| 9,486,155 B2 | 11/2016 | Sarkar et al. | |
| 2006/0235476 A1 | 10/2006 | Gunderson et al. | |
| 2008/0082014 A1 | 4/2008 | Cao et al. | |
| 2009/0018597 A1* | 1/2009 | Wenzel | A61B 5/02156 |
| | | | 607/23 |
| 2009/0270749 A1 | 10/2009 | Haluska | |
| 2009/0281587 A1 | 11/2009 | Pei | |
| 2011/0125206 A1 | 5/2011 | Bornzin et al. | |
| 2012/0029373 A1 | 2/2012 | Stadler et al. | |
| 2013/0066222 A1* | 3/2013 | Rosenberg | A61B 5/0468 |
| | | | 600/518 |
| 2013/0138005 A1 | 5/2013 | Dong et al. | |
| 2014/0350630 A1* | 11/2014 | Rosenberg | A61N 1/3688 |
| | | | 607/18 |
| 2015/0038863 A1 | 2/2015 | Schotten et al. | |
| 2016/0129263 A1* | 5/2016 | Demmer | A61N 1/3702 |
| | | | 607/17 |
| 2016/0213270 A1 | 7/2016 | Cao et al. | |
| 2017/0014629 A1* | 1/2017 | Ghosh | A61N 1/36507 |
| 2017/0251940 A1 | 9/2017 | Perschbacher et al. | |
| 2017/0273589 A1 | 9/2017 | Sarkar et al. | |
| 2018/0028086 A1* | 2/2018 | Cao | A61B 5/0432 |
| 2018/0028814 A1* | 2/2018 | Ghosh | A61N 1/3756 |
| 2018/0064360 A1 | 3/2018 | Siejko et al. | |
| 2018/0078773 A1* | 3/2018 | Thakur | A61B 5/4836 |
| 2018/0161572 A1* | 6/2018 | Gunderson | A61B 5/046 |

OTHER PUBLICATIONS

Extended European Search Report for corresponding EP Application No. 19172673.6 dated Jul. 15, 2019 (5 pages).

* cited by examiner

VENTRICULAR LEADLESS IMPLANTABLE MEDICAL DEVICE WITH DUAL CHAMBER SENSING AND METHOD FOR SAME

FIELD

Embodiments generally relate to implantable medical devices, and more particularly to single-chamber leadless implantable medical devices configured to provide dual-chamber sensing.

BACKGROUND

Current small implantable medical devices (IMD) for cardiac applications, such as pacemakers, are provided to be entirely implanted within a chamber of the heart. The small IMD is also referred to as a leadless IMD or LIMD. LIMDs do not include a lead and generally are configured to sense only cardiac activity (CA) signals in connection with the chamber, in which the LIMD is implanted. For example, a LIMD implanted in the right atrium would primarily sense right atrial cardiac activity, while a LIMD implanted in the right ventricle would primarily sense right ventricular cardiac activity.

A LIMD device that is located in the right atrium would generally be limited to offering AAI mode functionality, while another LIMD that is located in the right ventricle would be limited to offering VVI mode functionality. A VVI mode LIMD can only sense in the right ventricle, pace in the right ventricle and inhibit pacing function when an intrinsic event is detected in the right ventricle within a preset time limit. To gain widespread acceptance by clinicians, it would be highly desired for a LIMD to have dual chamber sensing capability along with other features, such as rate adaptive pacing.

Leadless IMDs have been associated with reduced clinical complications relative to traditional pacemakers with transvenous leads. Although standard single-chamber ventricular leadless pacemakers have demonstrated success as VVI devices, they are unable to sense and track the intrinsic atrial rhythm. While temperature sensors and accelerometers may be employed for rate-responsive VVIR devices, properly leveraging the atrial "kick" in real-time requires actively monitoring the electrical activity in the atria (i.e., identifying P-waves) and timing ventricular pacing pulses accordingly. A need remains for a LIMD and method to identify far-field P-waves from the intracardiac electrocardiogram (EGM) signals collected by ventricular leadless pacemakers to synchronize ventricular pacing with the atrial rhythm.

SUMMARY

In accordance with one embodiment, methods and systems are provided to identify far-field P-waves from the intracardiac electrocardiogram (EGM) signals collected by a ventricular LIMD to synchronize ventricular pacing with an atrial rhythm. The methods and systems detect far-field atrial P-waves using the EGM signal observed by a ventricular LIMD. A P-wave template waveform is first established in connection with a window of the ventricular EGM. Subsequently, the incoming EGM is continually compared with the P-wave template in real-time, A P-wave is successfully identified (e.g., "sensed") when the incoming signal sufficiently matches the P-wave template, as quantified by a set of pre-defined thresholds (e.g., cross-correlation coefficient, signal amplitude, frequency distribution, etc.). With sensed P-waves, the single-chamber, LIMD can, function in VDD mode to continuially track the atrial rhythm and provide synchrony via programmable sensed AV delay values.

In accordance with embodiments herein, a computer implemented method for providing dual chamber sensing with a single chamber leadless implantable medical device (LIMD) is provided. The method is under control of one or more processors in the LIMD configured with specific executable instructions. The method obtains a far field (FF) cardiac activity (CA) signals for activity in a remote chamber of a heart and compares the far field CA signals to a P-wave template to identify an event of interest associated with the remote chamber. The method sets an atrial-ventricular (AV) delay based on the P-wave identified and delivers pacing pulses at a pacing site of interest to a local chamber based on the AV delay.

Optionally, the P-wave template may be defined from an ensemble of FF CA signals, within a P-wave search window, for multiple beats. The method may form the P-wave template during an in-clinic feature set up that comprises for multiple beats obtaining surface ECG signals in parallel with calibration far field CA signals and based on the ECG signals aligning a P-wave search window within the calibration far field CA signals. The method may combine segments of the calibration FF CA signals aligned with the P-wave search window for the corresponding multiple beats to form the P-wave template. The P-wave search window may be defined, based on the ECG signals, manually or automatically.

Optionally, the P-wave search window may be formed automatically and may be aligned with the calibration FF CA signals a predetermined time interval prior to an R-wave in the calibration FF CA signals. The comparing operation may comprise determining at least one of a correlation or root-mean-square relation of between the P-wave template and the FF CA signal. The LIMD may be implanted in a right ventricle and the FF CA signals is indicative of cardiac events in the right atrium. The method may obtain a collection of P-wave templates associated with at least one of different atrial activity sources or different patient postures. The comparing operation may comprise comparing two or more of the collection of P-wave templates to the FF CA signals to account for different morphologies of a candidate P-wave in the FF CA signal.

Optionally, the FF CA signals and P-wave template may correspond to at least one an electrocardiogram (EGM) signal or a pressure signal. The method may repeatedly obtain samples for the FF CA signal and may save the samples in a first-in-first-out buffer to maintain a series of the samples from the FF CA signals for a P-wave search window. The series of the samples compared to the P-wave template may identify a P-wave as the event of interest.

In accordance with embodiments herein, a leadless implantable medical device (LIMD) is provided. The device comprises memory configured to store program instructions and a P-wave template. One or more processors, when executing the program instructions, are configured to obtain a far field (FF) cardiac activity (CA) signals for activity in a remote chamber of a heart and compare the far field CA signals to a P-wave template to identify an event of interest associated with the remote chamber. The device sets an atrial-ventricular (AV) delay based on the P-wave identified and delivers pacing pulses at a pacing site of interest to a local chamber based on the AV delay.

Optionally, the P-wave template may be defined from an ensemble of FF CA signals, within a P-wave search window, for multiple beats. The one or more processors may be further configured to form the P-wave template during an in-clinic feature set up that comprises for multiple beats may obtain surface ECG signals in parallel with calibration far field CA signals and based on the ECG signals may align a P-wave search window within the calibration far field CA signals. The processors may combine segments of the calibration FF CA signals aligned with the P-wave search window for the corresponding multiple beats to form the P-wave template.

Optionally, the P-wave search window is defined, based on the ECG signals, manually or automatically. The one or more processors may be further configured to identify an R-wave in the calibration FF CA signals. The processors may automatically form the P-wave search window and may align the P-wave search window with the calibration FF CA signals a predetermined time interval prior to the R-wave in the calibration FF CA signals. The one or more processors may be further configured to determine at least one of a correlation or root-mean-square relation of between the P-wave template and the FF CA signal.

Optionally, the LIMO may be configured to be implanted in a right ventricle and the FF CA signals is indicative of cardiac events in the right atrium. The one or more processors may be further configured to obtain a collection of P-wave templates associated with at least one of different atrial activity sources or different patient postures and may compare two or more of the collection of P-wave templates to the FF CA signals to account for different morphologies of a candidate P-wave in the FF CA signal.

Optionally, the FF CA signals and P-wave template may correspond to at least one an electrocardiogram (EGM) signal or a pressure signal. The one or more processors may be further configured to obtain repeated samples for the FF CA signal and may save the samples in a first-in-first-out buffer to maintain a series of the samples from the FF CA signals for a P-wave search window. The series of the samples compared to the P-wave template may identify a P-wave as the event of interest.

DETAILED DESCRIPTION

The term "leadless" shall mean an absence of transvenous and/or subcutaneous electrically-conductive leads that would otherwise traverse vessels or other anatomy inside or outside of an intra-cardiac space.

The term "intra-cardiac" shall mean entirely within the heart and/or associated vessels.

The term "adjacent chamber" shall refer to any chamber separated from a local chamber by tissue (e.g., the RV, LV and LA are adjacent chambers to the RA; the RA and LV are adjacent chambers to the LA; the RA and RV are adjacent to one another the RV and LV are adjacent to one another, and the LV and LA are adjacent to one another).

The term "real-time" shall refer to processing operations performed substantially contemporaneous with a physiological event of interest. By way of example, in accordance with embodiments herein, far field cardiac activity signals are analyzed in real time (e.g., during a cardiac event) to detect atrial activity for a cardiac beat, set an AV delay based on the atrial activity and deliver or inhibit a ventricular pacing pulse in connection with the same cardiac beat. In the foregoing example, "real-time" refers to processing and identifying the atrial event within the duration of a single heartbeat, such as during an AV delay.

For example, a typical pacing mode may include DDIR, R, DDOR and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or O). The code O is used when pacemaker discharge is not dependent on sensing electrical activity. The third letter refers to the response to a sensed electric signal (e.g., T: Triggering of pacing function; Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). The fourth letter indicates rate responsive if R is present.

Figure 1:
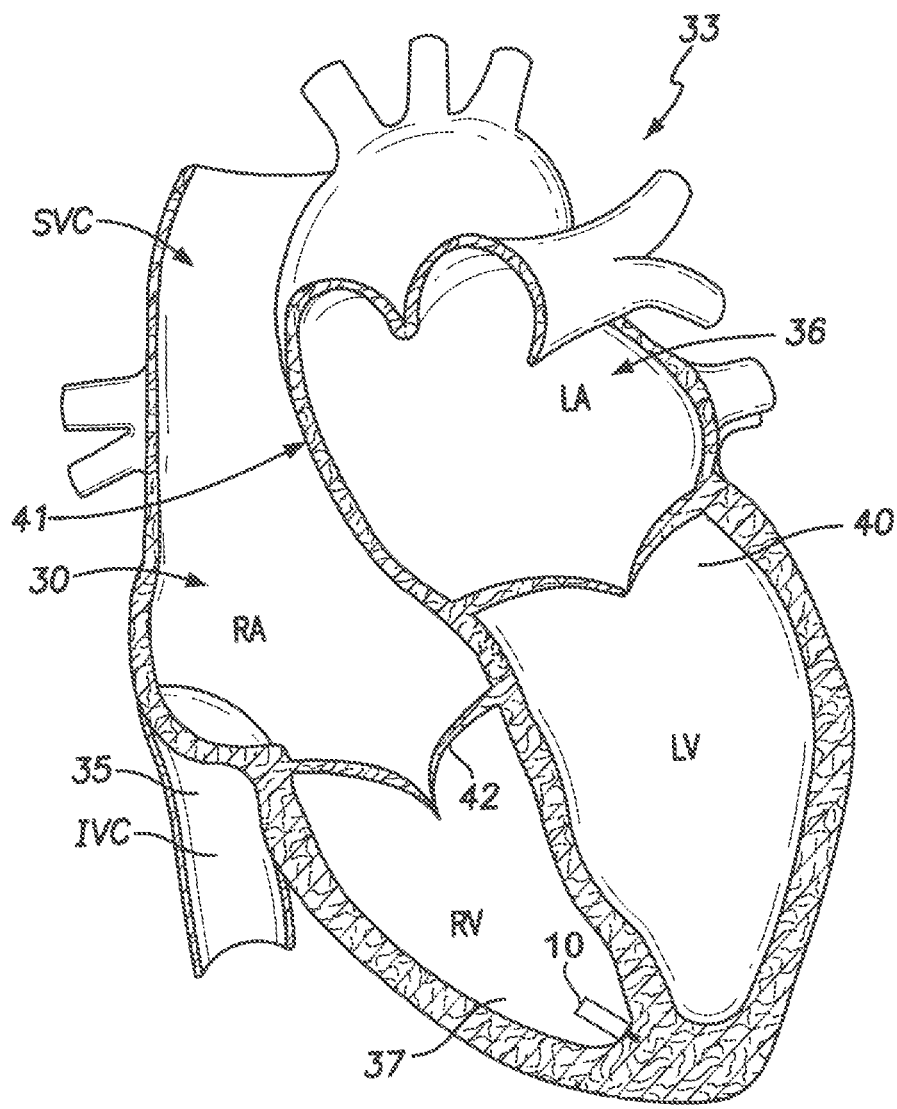
FIG. 1 provides a sectional view of a patient's heart and shows a leadless intra-cardiac medical device in accordance with embodiments herein.

FIG. 1 provides a sectional view of a patient's heart 33 and shows a leadless intra-cardiac medical device 10 (also referred to as a LIMD). FIG. 1 shows the inferior vena cava 35, the left atrium 36, the right ventricle 37, the left ventricle 40, the atrial septum 41 that divides the two atria 30, 36, the ventricular vestibule VV, the right atrial appendage (RAA), and the tricuspid valve 42 between the right atrium 30 and right ventricle 37. The leadless implantable medical device 10 has been placed proximate to the apex of the right ventricle 37 of the heart 33. The reader will appreciate that the view of FIG. 1 is simplified and somewhat schematic, but that nevertheless FIG. 1 and the other views included herein will suffice to illustrate adequately the placement and operation of embodiments of the present invention. The term "septum" shall be used throughout to generally refer to any portion of the heart separating two chambers (e.g., RA to LA, RV to LV). The leadless implantable medical device (LIMD) 10 is formed in accordance with an embodiment. The LIMD 10 may represent a pacemaker that functions in a VDD mode or a VDDR-mode, a cardiac resynchronization device, a cardioverter, a defibrillator and the like. When in VDD or VDDR-mode, the LIMD 10 may sense in two chambers, pace in one chambers and inhibit pacing based on intrinsic events sensed in that chamber or in the other chamber. The LIMD 10 comprises a housing configured to be implanted entirely within a single local chamber of the heart. For example, the LIMD 10 may be implanted entirely and solely within the right atrium or entirely and solely within the right ventricle. Optionally, the LIMD 10 may be implanted entirely and solely within the left atrium or left ventricle through more invasive implant methods.

For convenience, hereafter the chamber in which the LIMD 10 is implanted shall be referred to as the "local" chamber. The local chamber includes a local chamber wall that is physiologically response to local activation events originating in the local chamber. The local chamber is at least partially surrounded by local wall tissue that forms or constitutes at least part of a conduction network for the associated chamber. In the example of FIG. 1, the adjacent or remote chambers are the RA, LA and LV. During normal operation, the wall tissue of the right atrium contracts in response to an intrinsic local activation event that originates at the sinoatrial (SA) node (or another source) and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern continues from the AV node along the bundle of HIS and then into the Purkinje fibers which make up the left and right bundle branches; subsequently all ventricular muscle becomes activated. The bundle of HIS divides in the interventricular septum into right and left bundle branches. The right bundle branch branches off of the bundle of HIS and travels down the interventricular septum near the endocardium.

Figure 2:
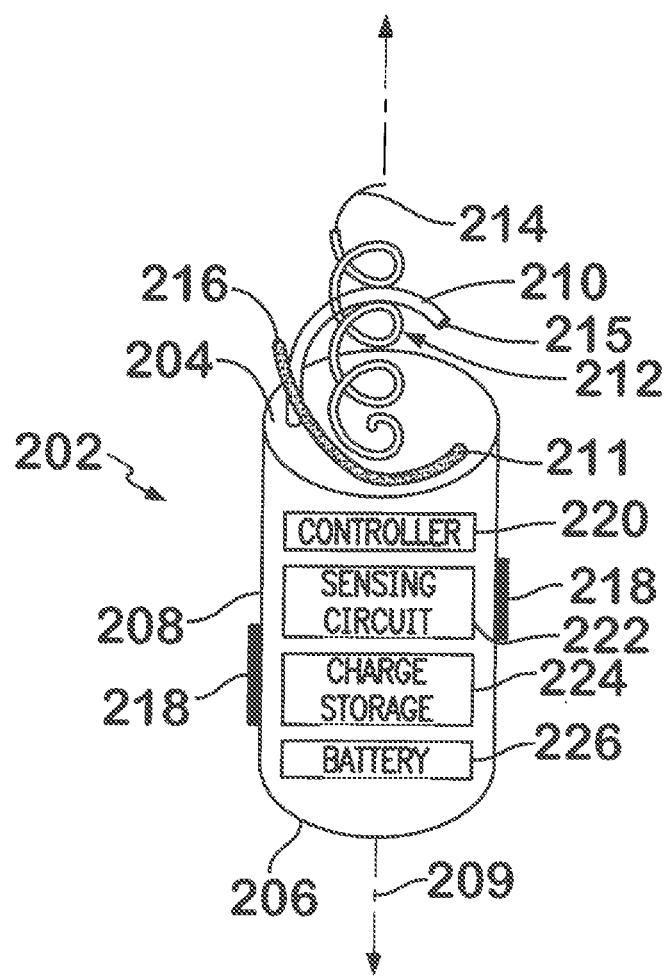
FIG. 2 illustrates a side perspective view of the LIMD oriented with the base facing upward to illustrate electrodes in more detail in accordance with embodiments herein.

FIG. 2 illustrates a side perspective view of the LIMD of FIG. 1 oriented with the base 204 facing upward to illustrate electrodes 210-212 in more detail. The LIMD 10 comprises a housing 202 having a proximal base 204, a distal top end 206, and an intermediate shell 208 extending between the proximal base 204 and the distal top end 206. The shell 208 is elongated and tubular in shape and extends along a longitudinal axis 209.

The base 204 includes one or more electrodes 210-212 securely affixed thereto and projected outward. For example, the outer electrodes 210, 211 may be formed as large semi-circular spikes or large gauge wires that wrap only partially about the inner electrode 212. The electrodes 210, 211 may be located on opposite sides of, and wound in a common direction with, the inner electrode 212. The first or outer electrodes 210, 211 are provided directly on the housing 202 of the LIMD 10 at a first position, namely at or proximate a periphery of the base 204 of the housing. The outer electrodes 210, 211 are positioned near the periphery of the base 204 such that, when the LAID 10 is implanted in the local chamber (e.g., right atrium), the outer electrodes 210, 211 engage the local chamber wall tissue at tissue of interest for a local activation site that is near the surface of the wall tissue, and that is within the conduction network of the local chamber. The outer electrodes 210, 211 are physically separated or bifurcated from one another and have separate distal outer tips 215, 216. The outer electrodes 210, 211 are electrically joined to one another (i.e., common), but are electrically separated from the inner electrode 212.

The second or inner electrode 212 is also provided directly on the housing 202 of the LIMD 10 at a second position, namely at or proximate to a central portion of the base 204 of the housing. The inner electrode 212 is positioned near the center of the base 204 and is elongated such that, when the LIMD 10 is implanted in the local chamber, the inner electrode 212 extends a majority of the way through the wall tissue (e.g., septum) until reaching tissue of interest near the adjacent chamber wall. The inner electrode, 212 is inserted to a depth such that a distal tip thereof is located at tissue of interest for an activation site that is physiologically coupled to wall tissue of the adjacent chamber (e.g., right ventricle). For example, the inner electrode 212 may extend until the distal tip extends at least partially through a septum to a position proximate to a distal wall tissue within the conduction network of the adjacent chamber. Optionally, the inner electrode 212 may be inserted at a desired angle until the distal end enters the ventricular vestibule. By located the distal tip of the inner electrode 212 at an adjacent chamber activation site, the inner electrode 212 initiates contraction at a distal activation site within the conduction network of the adjacent chamber without physically locating the LIMD 10 in the adjacent chamber. The inner and outer electrodes 210-212 may be formed as multiple cathode electrodes that are actively fixated to the myocardium. The outer cathode electrodes 210, 211 may be configured as screws with a large pitch (e.g., length between adjacent turns), large diameter and may have a length that is relatively short, while the inner electrode 212 is configured as a screw with a common or smaller pitch, small diameter and longer length. The screw shape of the outer electrodes 210, 211 is used to firmly adhere them to the cardiac tissue. The outer electrodes 210, 211 may have very little or no insulation material thereon to facilitate a good electrical connection to local wall tissue along the majority or the entire length of the outer electrodes 210, 211 for delivering stimulus pulses and sensing electrical activity in the local chamber where the LIMD 10 is located.

The inner electrode 212 is shaped in a helix or screw and is longer (e.g., extends a greater distance from the base) than the outer electrodes 210, 211. The inner electrode 212 is fashioned to an appropriate length that permits it to drill a predetermined distance into, or entirely through, the septum at the desired location. For example, the inner electrode 212 may be provided with a desired length sufficient to extend through, or to a desired distance into, a septum region separating two chambers of the heart. For example, the outer electrodes 210, 211 may contact ventricular wall tissue within the triangle of Koch, while the inner electrode 212 extends diagonally along the septum into the ventricular vestibule.

The inner electrode 212 may be formed as a single conductive wire or a bundle of conductive wires, where a proximal portion of the wire is covered with insulation, while the distal tip 214 is covered with insulation and is exposed. By covering the proximal portion of the electrode 212 with insulation, this limits electrical conduction of the conductive wire to tissue surrounding the distal tip 214. When implanted, the distal tip 214 of the electrode is located far below the surface tissue of the chamber wall in which the LIMD 10 is located. As a consequence, the distal tip 214 of the inner electrode 212 directly engages or is located proximate to the surface tissue of an adjacent chamber wall. Hence, the distal tip 214 senses electrical activity from the conductive network of the adjacent chamber that is representative of physiological behavior (e.g., conduction pattern) of the adjacent chamber. Also, when delivering stimulus pulses, the distal tip 214 will deliver the pulses into the conductive network of the adjacent chamber wall.

The combination of the inner and outer screw type electrodes 210-212 also imparts extra mechanical stability to the LIMD 10, preventing unwanted torque and shear effects as the heart wall moves during contraction. Otherwise, such effects would otherwise predispose the LIMD 10 to dislodgement. Extraction could simply entail a combination of unscrewing of the two cathodes in conjunction with a slight tugging force directed away from the myocardial wall.

Optionally, a single anode electrode or multiple anode electrodes 218 may be provided. The anode electrode(s) 218 may be located along one or more sides of the shell 208, and/or on the top end 206 of the LIMD 10.

The LIMD 10 includes a charge storage unit 224 and sensing circuit 222 within the housing 202. The sensing circuit 222 senses intrinsic activity, while the charge storage unit 224 stores high or low energy amounts to be delivered in one or more stimulus pukes. For example, the sensing circuit 222 may define a near field sensing channel and a far field sensing channel. The near field and far field sensing channels may be processed with different low-pass filters, high pass filters, amplifiers and the like. By way of example, the far field sensing channel may implement bipolar sensing that utilizes a band pass filter with a bandwidth of 0.5-100 Hz, the output of which includes the FF CA signals. The bipolar sensing is implemented between distal and proximal electrodes provided on the LIMD. Additionally, the sensing circuitry may include an AC noise notch filter that includes a notch that is centered at approximately 50-60 Hz, depending upon a local AC frequency.

The electrodes 210-212 may be used to deliver lower energy or high energy stimulus, such as pacing pukes, cardioverter puke trains, defibrillation shocks and the like. The electrodes 210-212 may also be used to sense electrical activity, such as physiological and pathologic behavior and events and provide sensed signals to the sensing circuit 222. The electrodes 210-212 are configured to be joined to an energy source, such as a charge storage unit 224. The electrodes 210-212 receive stimulus pulse(s) from the charge storage unit 224. The electrodes 210-212 may be the same or different size. The electrodes 210-212 are configured to deliver high or low energy stimulus pulses to the myocardium.

The LIMD 10 includes a controller 220, within the housing 202, to cause the charge storage unit 224 to deliver activation pulses through each of the electrodes 210-212 in a synchronous manner, based on information from the sensing circuit 222, such that activation pulses delivered from the inner electrode 212 are timed to initiate activation in the adjacent chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The inner and outer electrodes 210-212 are spaced radially and longitudinally apart from one another such that the local activation site (e.g., right atrium)) and the distal activation side in the adjacent chamber (e.g., right ventricle) are sufficiently remote from one another within the heart's conductive network to initiate activation in different branches of the hearts conductive network in a time relation that corresponds to the normal hemodynamic timers (e.g., AV delay).

The controller 220 implements the operations described herein. The controller 220 may operate the LIMD 10 in various modes, such as in select pacemaker modes, select cardiac resynchronization therapy modes, a cardioversion mode, a defibrillation mode and the like. The sensing circuit 222 receives sensed signals from one or more of the electrodes 210-212. The sensing circuit 222 discriminates between sensed signals that originate in the near field and in the far field. For example, the electrodes 210-211 sense electrical potential across small areas and thereby allow the sensing circuit 222 to discriminate between different sources of electrical signals. In one embodiment, the electrode spacing between electrodes 210, 211 is limited or minimized in order to achieve a select type of sensing such as bipolar sensing which limits or minimizes sensing of far field signals. For example, the electrode 210 may operate as an anode electrode and the electrode 211 may operate as a cathode electrode with a small separation there between such that when far field signals (e.g., signals from the right ventricle) reach the first and second electrodes these far field signals are sensed as a common mode signal with no or a very small potential difference between the electrodes.

Optionally, the LIMD 10 may include an accelerometer (e.g., a three-dimensional MEMS accelerometer) that, in combination with one or more processors of the controller 220, is configured to automatically determine a posture/orientation of the LIMD and patient. Posture measurements from the accelerometer may be utilized in connection with building different P-wave templates to be utilized in combination with different patient postures. The posture measurements from the accelerometer may also be used continuously in real time to identify the current posture of the patient and LIMD and based thereon enable the controller 220 to select a corresponding one or more of the P-wave templates to use with current FF CA signals.

In another example, an electrode 212 may be provided with a pair of electrically separate sensing regions thereon. The sensing regions may operate as an anode and as a cathode electrode with a small separation there between such that when far field signals (e.g., signals from the right atrium) reach the first and second sensing regions these far field signals are sensed as a common mode signal with no or a very small potential difference between the sensing regions. The housing 202 also include a battery 226 that supplies power to the electronics and energy to the charge storage unit 224.

The proposed atrial sensing feature to be implemented in ventricular LIMDs functions by (1) establishing a ventricular EGM P-wave template and (2) Comparing the template with the incoming ventricular EGM signal to identify incoming P-waves in real-time.

Figure 3:
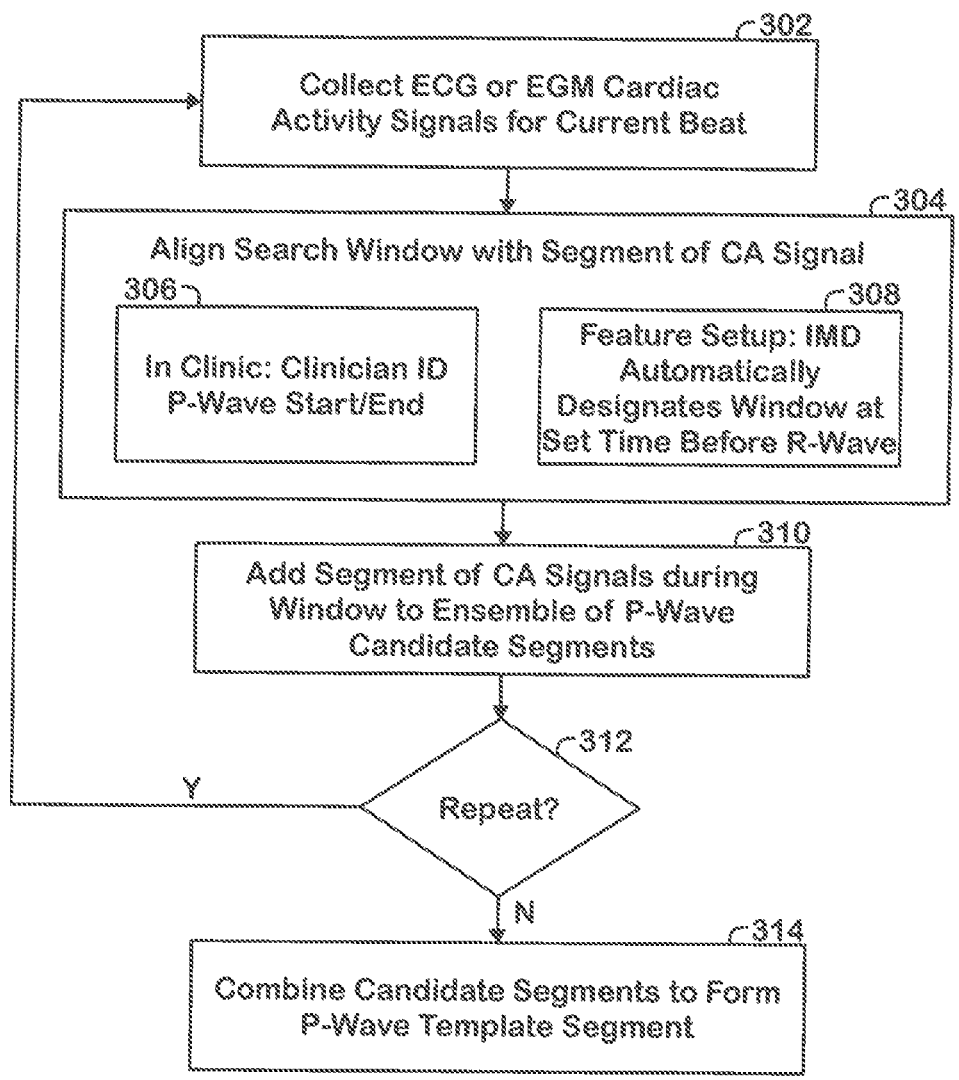
FIG. 3 illustrates a method to establish a P-wave template in accordance with embodiments herein.

FIG. 3 illustrates a method to establish a P-wave template in accordance with embodiments herein. The method of FIG. 3 may be implemented by one or more processors of the LIMO alone or in combination with one or more processors of an external device. Additionally or alternatively, at least a portion of the operations of FIG. 3 may be implemented by a programmer device under control of a clinician, such as when viewing ECG strips presented on a display.

At 302, the one or more processors manage collection of cardiac activity signals for a current beat of interest. The CA signals may represent ECG signals (e.g., when collected by surface ECG leads) and/or EGM signals (e.g., when collected by the electrodes on a LIMD).

At 304, the one or more processors align a search window with a segment of intracardiac far field CA signals for the current beat. For example, the search window may have a length corresponding to approximately 300 ms of the CA signal. The alignment may be implemented in alternative manners, two of which are illustrated in FIG. 3. For example, as noted at 306, during an in clinic visit, a clinician may operate an external programmer device to facilitate the alignment. For example, a surface ECG lead system connected to a programmer device may collect ECG signals, simultaneously and contemporaneously in real time, while a LIMD collects "calibration" FF CA signals (e.g., EGM signals) corresponding to the same cardiac beat(s). The ECG signals are displayed to the clinician (on a display of the programmer) who identifies one or more P-waves of interest on the ECG signals displayed in connection with the current one or more beats of interest. The clinician may identify start and end times for a P-wave, a peak of the P-wave and the like, in various manners. For example, the clinician may utilize various types of graphical user interfaces to identify start and end points along the ECG signals, to identify a peak of a P-wave, to identify a width of a P-wave and the like.

Once the clinician identifies the start and end times for the P-wave (or a peak of the P-wave) on the ECG signals displayed on the programmer, the programmer transmits corresponding window timing information to the LIMD. The LIMD utilizes the window timing information to define start and end times (and/or a center and width) for a search window along the calibration FF CA signals collected by the LIMD. The LIMD utilizes the start and end times to overlap the search window onto a segment of the calibration FF CA signals.

Additionally or alternatively, the alignment at 304 may be implemented entirely automatically by the LIMD. For example, as noted at 308, the alignment may be performed during a feature set up operation. For example, the LIMD may automatically define the search window and align the search window with a corresponding segment of calibration CA signals. As part of the automatic alignment, the LIMD may analyze a segment of the CA signals to identify a characteristic of interest from a ventricular event (e.g., a peak of the R-wave). Once the LIMD identifies the peak of the R-wave, the processors of the LIMD align the search window with a segment of the CA signals that precedes the R-wave peak by a predefined interval.

At 310, the one or more processors add the segment of the CA signals, corresponding to the search window, to a collection of P-wave candidate segments. At 312, the one or more processors determine whether a desired number of P-wave candidate segments for a desired number of beats have been collected. For example, it may be desired to combine CA signals segments for 5, 10 or more cardiac beats. At 314, the one or more processors combine the collection of P-wave candidate segments into an ensemble to form a P-wave template segment. The one or more processors may form the P-wave template segment in various manners utilizing various mathematical operations, such as through averaging (weighted or unweighted), means, medians and the like. For example, the P-wave template may be defined as a monophasic waveform with a 70 ms duration.

In accordance with the operations of FIG. 3, alternative methods are provided for establishing P-wave templates. When utilizing an in clinic feature set up (at 306), P waves are easily identified by a clinician while reviewing surface ECG strips displayed on the programmer. Additionally or alternatively, when utilizing an automatic feature set up (at 308), the process is based solely on the CA signals (EGM based signals). The automated process at 308 may be implemented at any time throughout operation of the LIMD, such as periodically or when certain criteria are identified. The automated process at 308 may be implanted without use of an external programmer. The process at 308 allows for the P-wave template to be repeatedly redefined (e.g., daily, weekly), thereby allowing the LIMD to adapt to gradual changes in P-wave morphology and/or P-wave amplitudes.

Figure 4:
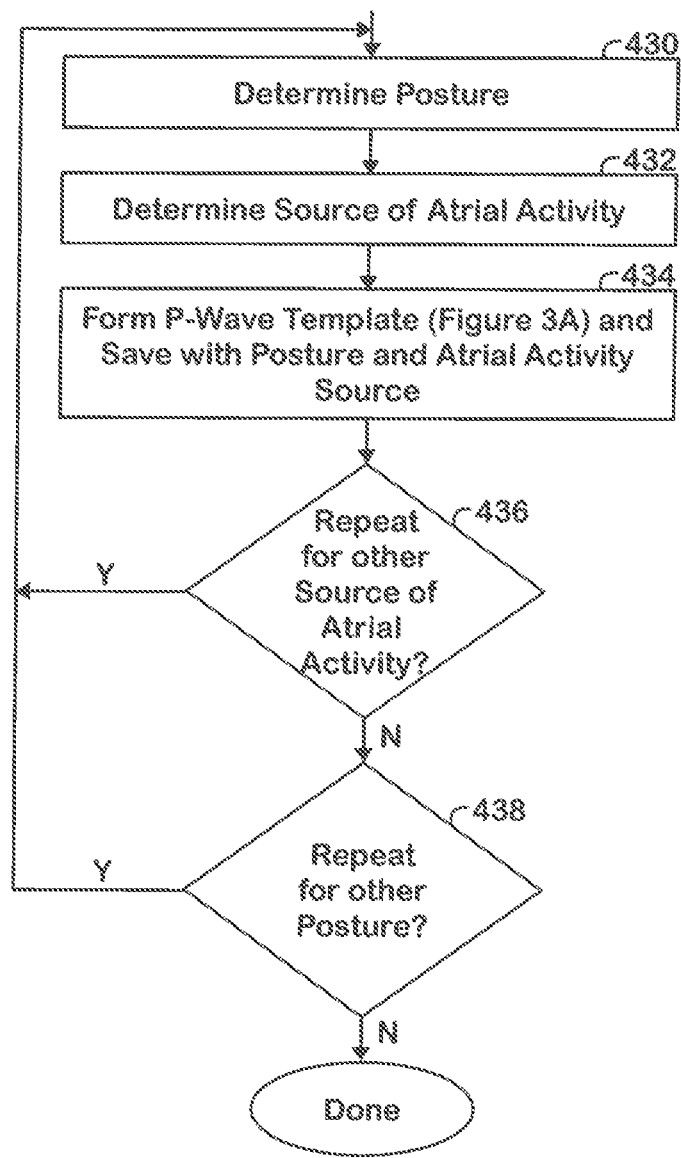
FIG. 4 illustrates a method to repeat the process of FIG. 3 to develop a collection of P-wave templates associated with different patient postures and/or different sources of atrial activity in accordance with embodiments herein.

FIG. 4 illustrates a method to repeat the process of FIG. 3 to develop a collection of P-wave templates associated with different patient postures and/or different sources of atrial activity in accordance with embodiments herein. Over time, a patient may experience different sources of atrial activity, such as atrial events originating from the SA node, ectopic focused atrial activity and the like. As the source of the atrial activity varies, the morphology of the P-wave detected in the FF CA signals may similarly vary. In accordance with embodiments herein, methods and systems account for all or multiple potential morphologies by building a collection of P-wave templates associated with different sources of atrial activity. Over time, the patient will shift between various postures that may introduce variations in the morphology of the P-wave detected in the FF CA signals. Accordingly, in accordance with embodiments herein, a patient may be directed to shift between different predefined postures, in connection with each of which, one or more P-wave templates may be formed in accordance with the process of FIG. 3.

With reference to FIG. 4, at 430, the one or more processors determine a current posture of the patient. The posture may be automatically determined by the LIMD based on measurements collected by an accelerometer within the LIMD (e.g, a three-dimensional MEMS accelerometer). Optionally, the posture may be determined based on communication with an external device. For example, a patient may be instructed to assume a position in a predetermined posture. The instruction may be provided by a clinician while operating a programmer. Additionally or alternatively, a local external device may provide an instruction to the patient, such as during a feature set up process automatically being implemented by the LIMD. When the patient has assumed the predetermined posture, the programmer or other local external device may convey the posture to the LIMD.

At 432, the one or more processors determine a current source of atrial activity. The source of atrial activity may be determined based on communication with an external device. For example, as part of an in clinic set up, a patient may be connected to an external ECG lead system. A clinician may manually identify the source of atrial activity based on visible inspection of the ECG strips displayed. Additionally or alternatively, the local programmer device may automatically identify the source of atrial activity from the ECG strips. The local external programmer may then wirelessly transmit the source of atrial activity to the MD. Additionally or alternatively, as part of an automated feature set up, the LIMD may analyze far field CA signals and determine one of multiple different sources of the atrial activity.

At 434, the one or more processors implement the process of FIG. 3 to form a P-wave template from a combination of candidate segments that are collected while the patient is in the predefined posture and/or while the patient is exhibiting atrial activity of the determined source. The P-wave template is also saved in connection with the corresponding posture and source of atrial activity.

At 436, the one or more processors determine whether to repeat the operations of FIG. 4 in connection with another source of atrial activity. If so, flow returns to 430 and the operations are repeated. If not, flow continues to 438. At 438, the one or more processors determine whether to repeat the operations of FIG. 4 in connection with another posture. If so, flow returns to 430 and the operations are repeated for a next predetermined posture.

While the operations of FIG. 4 are described in a somewhat interrelated sear manner in which P-wave templates are developed for multiple postures and for multiple sources of atrial activity in combination, it is understood that the operations related to posture based collection of P-wave templates may be performed entirely separate and independent of any collection of P-wave templates for atrial activity sources. For example, the operations at 432 and 436 may be omitted entirely, with the operations of FIG. 4 implemented only in connection with different postures. As another example, the operations at 430 and 438 may be omitted entirely, with the operations of FIG. 4 implement only in connection with different atrial activity sources.

Figure 5:
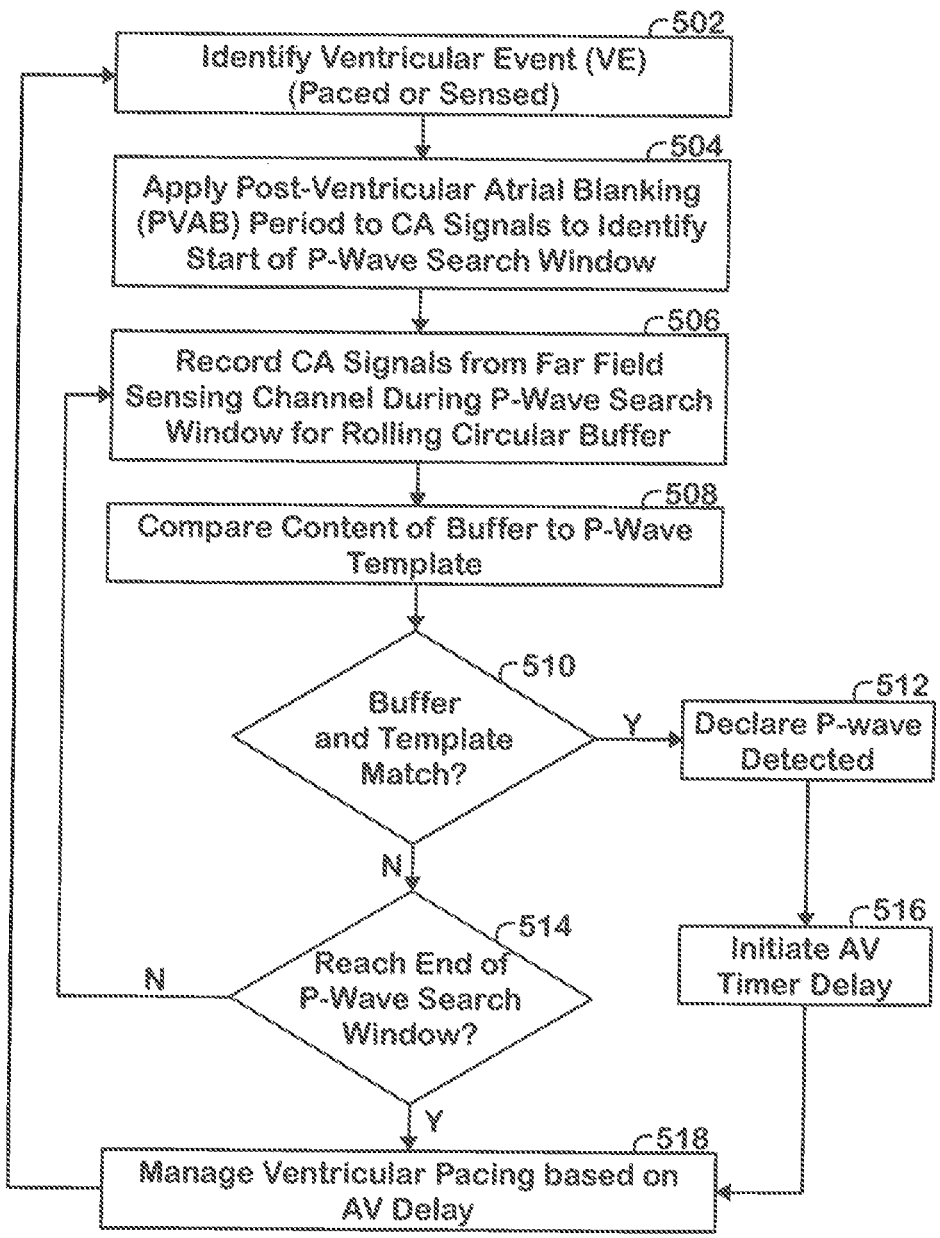
FIG. 5 illustrates a process for identifying atrial events based on far field CA signals in accordance with embodiments herein.

FIG. 5 illustrates a process for identifying atrial events based on far field CA signals in accordance with embodiments herein. The method of FIG. 5 may be implemented by one or more processors of the LIMD alone or in combination with one or more processors of an external device. At 502, the one or more processors identify a ventricular event (VE). The VE may be a paced or sensed VE. For example, the one or more processors may identify an intrinsic VE from prior CA signals. Alternatively, the one or more processors may identify a paced VE when the LIMO delivers a ventricular pacing pulse after an AV delay has timed out without an intervening intrinsic VE.

At 504, the one or more processors set a timer corresponding to a post ventricular atrial blanking (PVAB) period in order to skip a window of ventricular activation. During the PVAB period the one or more processors ignore incoming far field CA signals as no legitimate atrial event is expected during the PVAB period. The timer expires at the end of the PVAB period, thereby indicating that subsequent CA signals may potentially include a P-wave. Accordingly, at the end of the PVAB period the one or more processors open a P-wave search window.

At 506, the one or more processors begin recording FF CA signals from the far field sensing channel during the P-wave search window. The far field CA signals are stored in a rolling circular buffer the may have a desired length. For example, the P-wave search window may have a length of 300 ms or more, whereas the circular buffer may have a shorter length, such as 50-200 ms. As far field CA signals are recorded, the FF CA signals are loaded into the circular buffer in a first-in-first-out (FIFO) order. Once the circular buffer is filled, additional incoming far field CA signals are loaded into the circular buffer and written over the oldest far field CA signals in the circular buffer.

At 508, the one or more processors compare the present content of the circular buffer to the P-wave template segment formed in connection with the process of FIG. 3. The one or more processors may utilize a single common P-wave template in connection with all comparisons. Additionally or alternatively, the one or more processors may apply a collection of P-wave templates in parallel, where the present content of the circular buffer is compared in parallel to multiple P-wave templates. When multiple P-wave templates are utilized, the P-wave templates may correspond to templates formed based on different patient postures. For example, four separate patient postures may be defined (e.g., standing, prone, laying on the left side, laying on the right side). The processors may perform four comparisons in parallel applying the same current FF CA signals to each of the four P-wave templates in search of a match.

Additionally or alternatively, the one or more processors may receive information from an accelerometer or other sensor indicating the present posture of the patient, and choose one of the posture related P-wave templates for comparison with the current FF CA signals.

Additionally or alternatively, the one or more processors may apply a collection of P-wave templates that correspond to different sources of atrial activity. For example, multiple separate atrial activity sources may be defined (e.g., as node, ectopic focus). The processors may perform comparisons in parallel applying the same current FF CA signals to each of the atrial activity source related P-wave templates in search of a match. Additionally or alternatively, the one or more processors may analyze the incoming FF CA signals to identify an atrial activity source related thereto and choose one of the atrial activity source related P-wave templates for comparison with the current FF CA signals.

The recording at 506 and comparison at 508 are performed continuously, such that every time a new sample (or a desired number of samples) is loaded into the rolling circular buffer, the new content of the circular buffer is compared to the P-wave template at 508. Various techniques for applying the comparison are described herein, although it is recognized that other comparison techniques may be utilized additionally or alternatively (e.g., Kendall rank/ Kendall tau, Spearman's rank, etc.). By way of example, the comparison may implement a Pearson's correlation coefficient that is used to quantify an extent to which the most recent segment of FF CA signals in the circular buffer match the P-wave template.

At 510, the one or more processors determine whether the current FF CA signals content of the circular buffer match the P-wave template.

By way of example, the comparison between the incoming FF CA signals and the P-wave template may be continuously compared until a match is found. For example, the Pearson's correlation coefficient may be implemented as follows:

$$r = \frac{\sum_{i=1}^{n}(x_i - \bar{x})(y - \bar{y})}{\sqrt{\sum_{i=1}^{n}(x_i - \bar{x})^2}\sqrt{\sum_{i=1}^{n}(y_i - \bar{y})^2}}$$

In the above equation, r is the Pearson's correlation coefficient, n is the sample size of the P-wave template, x represents a series of samples defining the P-wave template signal (with mean $\tilde{x}$), and y is the current FF CA signals content of the circular buffer (with mean $\tilde{y}$). In connection with 510, the predefined threshold (as described herein) may be defined. Once the "template vs. buffer" correlation coefficient exceeds the predefined threshold (e.g., >0.9), the process determines that a match occurs, namely an atrial sensed event is detected from the FF CA signals content of the buffer.

Additionally or alternatively, the comparison may analyze a root-mean-square (RMS) of the current FF CA signals content in the circular buffer as compared to the P-wave template to further increase an accuracy of the P wave detection, as follows:

$$X_{rms} = \sqrt{\frac{1}{n}\sum_{i=1}^{n} x_i^2}$$

$$Y_{rms} = \sqrt{\frac{1}{n}\sum_{i=1}^{n} y_i^2}$$

In the above equation, n is the sample size of the P-wave template, x represents a series of samples defining the P-wave template signal, and y is the current FF CA signals content of the circular buffer. The values $X_{rms}$ and $Y_{rms}$ are RMS of the P-wave template and current FF CA signals in the buffer, respectively. The ratio $R_{rms} = Y_{rms}/X_{rms}$ is used to evaluate the similarity of an amplitude of the buffer content to an amplitude of the P-wave template.

In connection with 510, the predefined threshold (as described herein) may be defined. Once the "template vs. buffer" correlation coefficient exceeds the predefined threshold, and the $R_{rms}$ is within a predefined range (e.g., 0.5-1.5), the process determines that a match occurs, namely an atrial sensed event is detected from the FF CA signals content of the buffer.

Additionally or alternatively, the root-mean-square (RMS) of the difference ($E_{rms}$) between the incoming FF CA signals and the P-wave template may be used for the P wave detection.

$$E_{rms} = \sqrt{\frac{1}{n}\sum_{i=1}^{n}(x_i - y_i)^2}$$

In the above equation, n is the sample size of the P-wave template, x represents a series of samples defining the P-wave template signal, and y is the current FF CA signals content of the circular buffer. Once the RMS of the difference between "template vs. buffer", $E_{rms}$, is within a predefined range (e.g., <0.2), the process may determine, at 510, that an atrial sensed event is detected.

Optionally, the determination at 510 may implement, and rely one, either or both of the calculations of the RMS and RMS difference. The determination at 510 may be based on one independent criteria (e.g., from the various criteria described herein) or a combination of criteria (e.g., a combination of the criteria described herein).

Before a P-wave template "match" can be prospectively identified, the detection threshold (e.g., a correlation coefficient threshold) is established/calibrated during a set up operation. As one example, the detection threshold may be preprogrammed by a clinician or at the time of manufacture and/or implant of the LIMD. Additionally or alternatively, the detection threshold may be remotely updated periodically throughout operation, such as from remote instructions delivered to a LIMD from a local external device and/or a remote server. Additionally or alternatively, the LIMD may implement an internal detection threshold set up operation, during which the LIMD enters a VVI pacing mode for a desired period of time (e.g., 30+sec). During the VVI pacing mode, the LIMD consistently delivers ventricular paced events (unless an intrinsic ventricular event is sensed) at a defined interval. While the LIMD maintains the VVI pacing mode, the LIMD the calculates "template vs. buffer" comparison in the background. The patient-specific detection threshold can be defined based on the range of coefficients or RMS calculated over 20+ representative (e.g., non-ectopic) beats. For example, the detection threshold=minimum+ [maximum−minimum]/10. Once the detection threshold has been defined, the LIMD switches back to a VDD mode and provides ventricular pacing to track the atrial rate based on a programmed or automatically defined AV delay.

With continued reference to FIG. 5, when a match occurs, flow moves to 512. When a match does not occur, flow moves to 514. At 512, the one or more processors declare the far field CA signals to include a P-wave. At 516, the one or more processors initiate an AV delay timer. The AV delay timer is permitted to expire while the one or more processors monitor a near field channel for an intrinsic ventricular event. At 518, the one or more processors manage ventricular pacing based on the AV delay and the presence or absence of an intrinsic ventricular event before the AV timer expires. In the event an intrinsic ventricular event does not occur before the AV timer expires, the LIMD delivers a ventricular pacing pulse that tracks a desired timing with respect to the intrinsic atrial event detected from the far field CA signals. It is recognized that a relatively short "processing" delay occurs from a point in time when 1) when the physiological activity in the atrium occurred giving rise to the far field CA signals (associated with a P-wave), until 2) the initiation of the AV timer at 516. The length of time associated with the "processing" delay may be predetermined and accounted for within the duration of the AV delay timer set at 516. For example, the processing delay between the actual occurrence of the 1) atrial physiological activity and 2) initiating the AV delay timer may correspond to several microseconds or up to 1 ms. Accordingly, the AV delay timer may be adjusted accordingly to account for the fact that the processing delay occurred before the AV delay timer was initiated.

The operations at 510-518 detect a P-wave from far field CA signals and utilize the detected P-wave to initiate an AV timer in connection with providing ventricular pacing therapy. With sensed P-waves, the single-chamber, LIMD can function in VDD mode to continually track the atrial rhythm and provide synchrony via programmable sensed AV delay values.

Returning to 510, when the content of the buffer and the P-wave template segment do not match, flow moves to 514. At 514, the processors determine whether the search has reached the end of the P-wave search window. For example, the processors may continue to search for a P-wave until a time period expires associated with a base rate for an RR interval. The base rate for the RR interval may be defined to ensure that the LIMD maintains a base ventricular pacing rate that delivers ventricular pacing pulses when no atrial events are sensed.

If the end of the P-wave search window has not been reached, flow returns to 506, where additional far field CA signals are recorded, added to the circular buffer and analyzed at 508-510. Alternatively, at 514, when the end of the P-wave search window is reached, flow moves to 518. When flow moves from 514 to 518, the process determines that an atrial event was not detected (e.g., did not occur) during the time period in which a P-wave should have been detected. Accordingly, the one or more processors manage the ventricular pacing therapy for the next heartbeat based on an absence of an intrinsic atrial event. At 518, the one or more processors either deliver a ventricular pacing pulse or sense the presence of an intrinsic ventricular event before the AV delay times out. Following a paced or intrinsic ventricular event, flow returns to 502 and the process is repeated for the next cardiac beat.

Depending on the source of the atrial activity (e.g., SA node, ectopic focus), multiple P-wave morphologies may exist. To account for potential different P-wave morphologies, embodiments herein develop and store multiple P-wave templates. Embodiments herein then may apply one or more of the different P wave templates in parallel or in series to the incoming FF CA signals.

The P-wave identification methods and systems described herein are not limited to analyses of ventricular EGM signals. Optionally, LIMDs may be implemented as, or operated in combination with, intracardiac pressure sensors. The methods and systems described herein may be implement to define one or more atrial pressure templates. Once the templates are defined, the methods and systems herein may monitor real time far field atrial pressure signals and utilize various comparison algorithms (e.g., Cross-correlation) to compare the atrial pressure template and current far field atrial pressure signals and identify matches there between. The far-field atrial pressure signals may have higher signal-to-noise ratios in the ventricular pressure signed as compared to the ventricular electrical signal.

Figure 6:
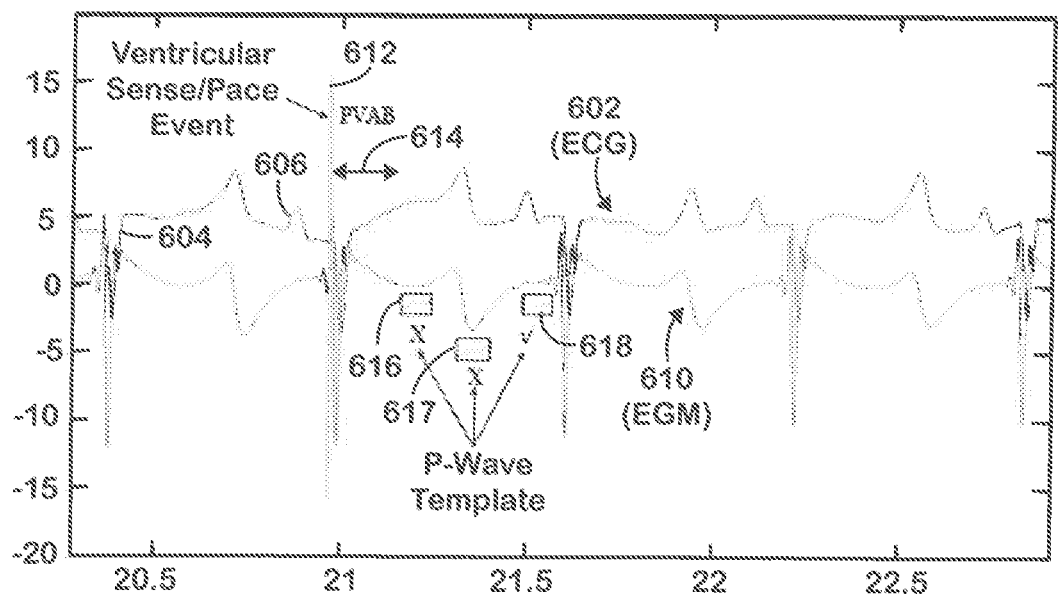
FIG. 6 illustrates an example of ECG signals and EGM signals collected and analyzed in accordance with embodiments herein.

FIG. 6 illustrates an example of ECG signals and EGM signals (corresponding to FF CA signals) collected and analyzed in accordance with embodiments herein. In FIG. 6, the ECG signal 602 is shown to include approximately four beats with corresponding R-waves 604 and P-waves 606. The EGM signals 610 include a ventricular sense/pace event 612 that would be identified at 602 (FIG. 5). Thereafter, a PVAB period 614 is applied (at 504), during which the process does not record nor analyze CA signals. Upon expiration of the PVAB period 614, the process begins recording the CA signals from the far field sensing channel. A series of rectangular blocks 616-618 are illustrated in FIG. 6 as examples of segments of the CA signals that are loaded into the circular buffer and compared to one or more P-wave templates at 508. An "X" is provided next to two of the rectangular blocks 616, 617 to indicate that the corresponding segments of the FF CA signals, when compared to the P-wave template, did not result in a match. A "checkmark" is provided next to the third rectangular block 618 to indicate that the corresponding segment of the FF CA signals, when compared to one or more P-wave templates, resulted in a match (at 510) and a declaration of a detected P-wave at 512.

Figure 7:
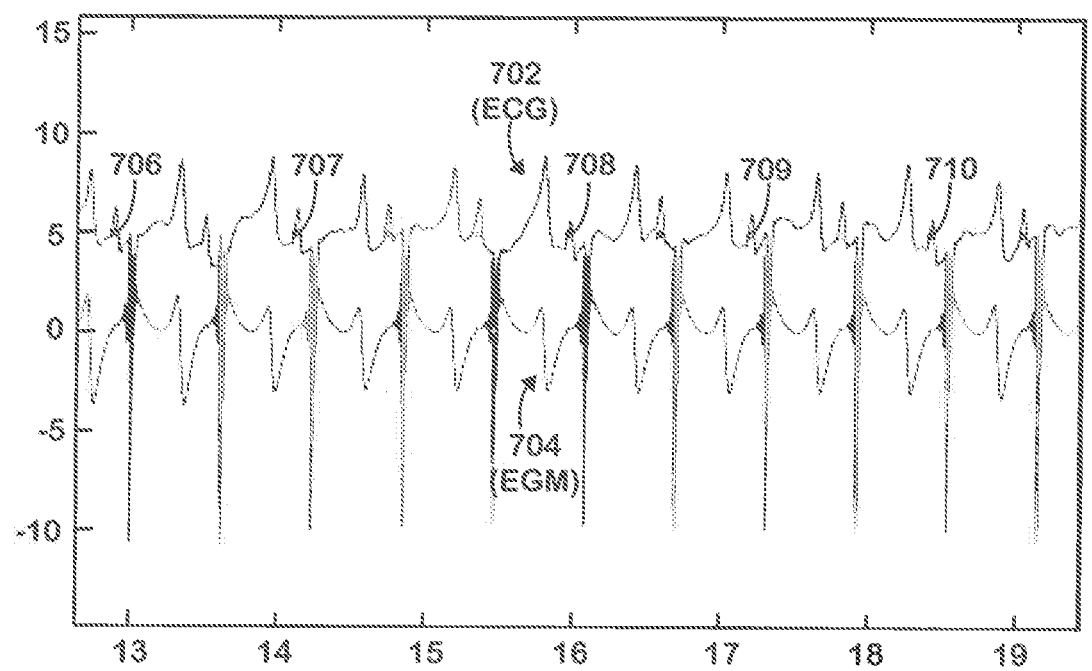
FIG. 7 illustrates an example of ECG signals and EGM signals analyzed in accordance with embodiments herein.

FIG. 7 illustrates an example of ECG signals and EGM signets analyzed in accordance with embodiments herein. And ECG signal 702 is collected by the lead H from a 12 lead ECG system. The EGM signal 704 represents and EGM signals collected over a far field bipolar sensing channel at the right ventricular apex. A series of stars 706-710 are plotted on the ECG signal 702 to indicate P waves that were identified in accordance with the methods and systems described herein using the EGM signal alone.

LIMD Block Diagram

Figure 8:
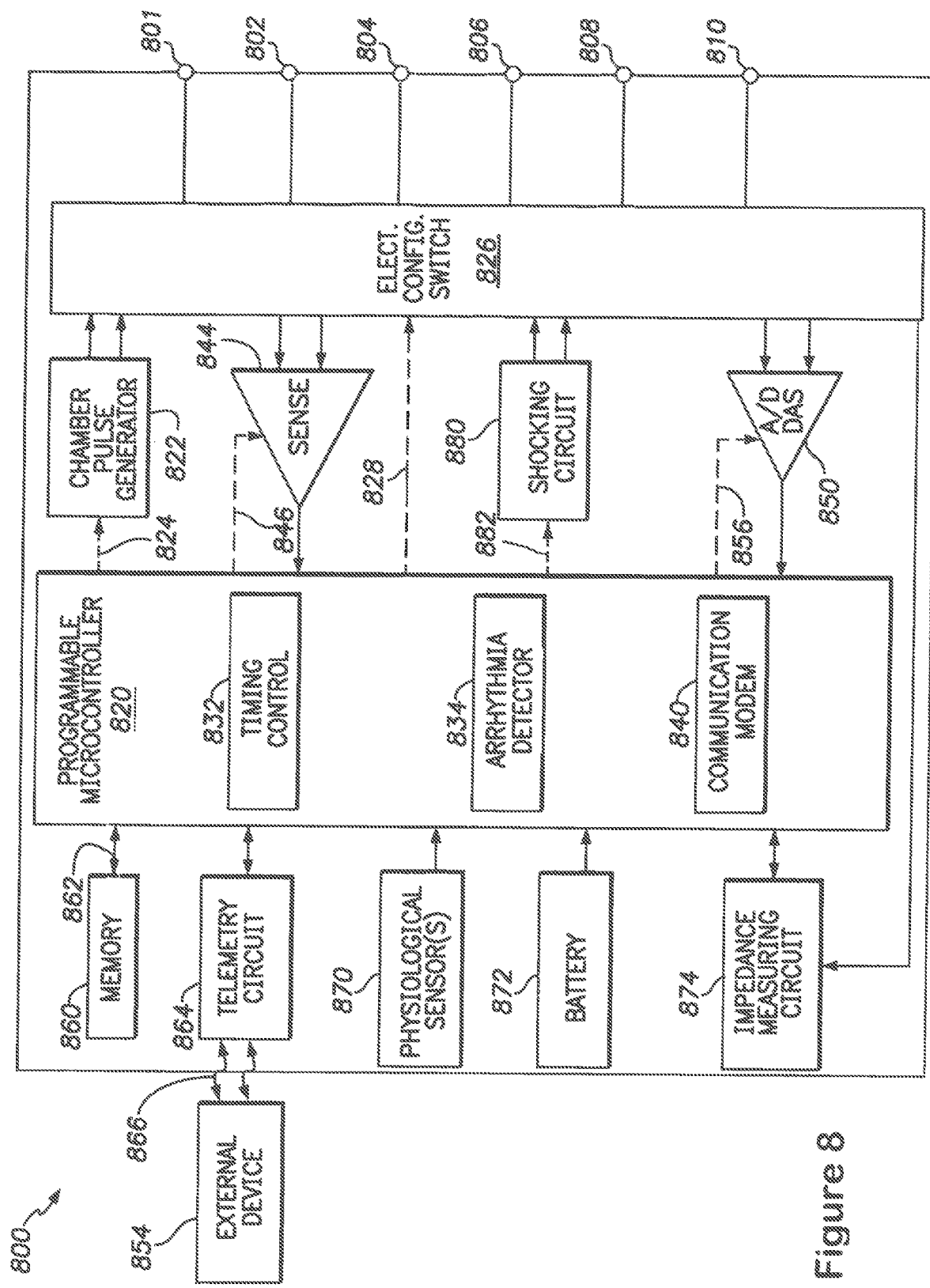
FIG. 8 shows an exemplary LIND configured for dual-chamber functionality from a primary location within a single chamber of the heart in accordance with embodiments herein.

FIG. 8 shows an exemplary LIMD 800 configured for dual-chamber functionality from a primary location within a single chamber of the heart. For example, the LIMD 800 may be implemented as a pacemaker, equipped with both atrial and ventricular sensing and pacing circuitry. Alternatively, the LIMD 800 may be implemented with a reduced set of functions and components. For instance, the LIMD 800 may be implemented without ventricular sensing and pacing. The LIMD 800 may also be implemented with an increased set of functions. For example, if the LIMD 800 includes a coil type electrode, the LIMD may be configured to include cardioversion and/or shocking therapy capability.

The LIMD 800 has a housing 801 to hold the electronic/computing components. The housing 801 (which is often referred to as the "can", "case", "encasing", or "case electrode") may be programmably selected to act as the return electrode for certain stimulus modes. Housing 801 further includes a plurality of terminals 802, 804, 806, 808, 810 that interface with electrodes of the LIMD. For example, the terminals may include: a terminal 802 that connects with a first electrode associated with the housing and located in a first chamber; a terminal 804 that connects with a second electrode associated with the housing and also located in the first chamber; a terminal 806 that connects with a third electrode associated with the housing and located in the first chamber and possibly partially extending into tissue associated with a second chamber; and two additional terminals 808, 810 that connect with one or more additional electrodes (e.g., electrode), if available. The type and location of each electrode may vary. For example, the electrodes may include various combinations of ring, tip, coil and shocking electrodes and the like.

The LIMD 800 includes a programmable microcontroller 820 that controls various operations of the LIMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry.

LIMD 800 further includes a first chamber pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate UO circuits, thereby facilitating electrode programmability. The switch 826 is controlled by a control signal 828 from the microcontroller 820.

In the example of FIG. 8, a single pulse generator 822 is illustrated. Optionally, the LIMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 800 includes sensing circuitry 844 selectively coupled to one or more electrodes through the switch 826. The sensing circuitry detects the presence of cardiac activity in the right chambers of the head. The sensing circuitry 844 may include dedicated sense amplifiers. Multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the example of FIG. 8, a single sensing circuit 844 is illustrated. Optionally, the LIMO 800 may include multiple sensing circuit, similar to sensing circuit 844, where each sensing circuit is coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 800 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The memory 860 also stores P-wave templates and program instructions to implement the comparisons between P-wave templates and incoming FF CA signals as described herein.

The operating parameters of the LIMD 800 may be non-invasively programmed into the memory 860 through a telemetry circuit 864 in telemetric communication via communication link 866 with the external device 854. The telemetry circuit 864 allows intracardiac electrograms and status information relating to the operation of the LIMD 800 (as contained in the microcontroller 820 or memory 860) to be sent to the external device 854 through the established communication link 866.

The LIMD 800 can further include magnet detection circuitry (not shown), coupled to the microcontroller 820, to detect when a magnet is placed over the unit. A magnet may be used by a clinician to perform various test functions of the unit and/or to signal the microcontroller 820 that the external programmer 854 is in place to receive or transmit data to the microcontroller 820 through the telemetry circuits 864. Optionally, the telemetry circuit 864 may be utilized to stream, in real time, incoming FF CA signals to a local external device and/or to a note the implantable medical device which in turn analyzes the FF CA signals as described herein. The local external device and/or other implantable medical device may then return instructions through the telemetry circuit 864 to instruct the LIMD to set an AV delay and/or deliver ventricular pacing pulses in connection with a ventricular pacing therapy. Optionally, the telemetry circuit 864 may implement i2i communication with another LIMD and/or subcutaneous IMD, wherein the communication may include the incoming FF CA signals, the results of the analysis (at 508-510) and the like.

The LIMD 800 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMO electrodes, such as between the can and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The LIMD 800 can further include one or more physiological sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and ventricular pacing pulses are administered. While shown as being included within the unit, the physiological sensor(s) 870 may be external to the unit, yet still be implanted within or carried by the patient. Examples of physiological sensors might include sensors that, for example, sense respiration rate, pH of blood, ventricular gradient, activity, position/posture, temperature, minute ventilation (MV), and so forth.

Optionally, the physiological sensor 870 may be configured to automatically determine a posture/orientation of the LIMD and patient. Posture measurements from the accelerometer may be utilized in connection with building different P-wave templates to be utilized in combination with different patient postures. The posture measurements from the accelerometer may also be used continuously in real time to identify the current posture of the patient and LIMD and based thereon enable the microcontroller 820 to select a corresponding one or more of the P-wave templates to use with current FF CA signals.

A battery 872 provides operating power to all of the components in the LIMD 800. The battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the unit employs lithium/silver vanadium oxide batteries.

The LIMD 800 further includes an impedance measuring circuit 874, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth. The impedance measuring circuit 874 is coupled to the switch 826 so that any desired electrode may be used.

The microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., up to 40 joules), as controlled by the microcontroller 820. Such shocking pulses are applied to the patient's heart through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that a LIMD may be used within a system that includes backup shock capabilities, and hence such shock therapy circuitry may be included in the LIMD.

What is claimed is:

1. A computer implemented method for providing dual chamber sensing with a single chamber leadless implantable medical device (LIMD) having electrodes provided on a housing of the LIMD, the LIMD implanted in a local chamber, comprising:
    under control of one or more processors in the LIMD configured with specific executable instructions,
    utilizing the electrodes to sense far field (FF) cardiac activity (CA) signals for activity in a remote chamber of a heart;
    comparing the far field CA signals to a P-wave template to identify a P-wave as an event of interest associated with the remote chamber, wherein the P-wave template is defined from an ensemble of FF CA signals, within a P-wave search window, for multiple beats;
    setting an atrial-ventricular (AV) delay based on the P-wave identified; and
    delivering pacing pulses, utilizing the electrodes, at a pacing site of interest in the local chamber based on the AV delay.

2. The method of claim 1, further comprising forming the P-wave template during an in-clinic feature set up that comprises:
    for multiple beats,
        obtaining surface ECG signals in parallel with calibration far field CA signals; and
        based on the ECG signals aligning a P-wave search window within the calibration far field CA signals; and
    combining segments of the calibration FF CA signals aligned with the P-wave search window for the corresponding multiple beats to form the P-wave template.

3. The method of claim 2, wherein the P-wave search window is defined, based on the ECG signals, manually or automatically.

4. The method of claim 2, wherein the P-wave search window is formed automatically and is aligned with the calibration FF CA signals by a predetermined time interval prior to an R-wave in the calibration FF CA signals.

5. The method of claim 1, wherein the comparing operation comprises determining at least one of a correlation or root-mean-square relation of between the P-wave template and the FF CA signal.

6. The method of claim 1, wherein the LIMD is implanted in a right ventricle and the FF CA signals are indicative of cardiac events in the right atrium.

7. The method of claim 1, further comprising obtaining a collection of P-wave templates associated with at least one of different atrial activity sources or different patient postures, the comparing operation further comprising comparing two or more of the collection of P-wave templates to the FF CA signals to account for different morphologies of a candidate P-wave in the FF CA signal.

8. The method of claim 1, wherein the FF CA signals and P-wave template correspond to at least one an electrocardiogram (EGM) signal or a pressure signal.

9. The method of claim 1, further comprising:
    repeatedly obtaining samples for the FF CA signal; and
    saving the samples in a first-in-first-out buffer to maintain a series of the samples from the FF CA signals for a P-wave search window, the series of the samples compared to the P-wave template to identify the P-wave as the event of interest.

10. A leadless implantable medical device (LIMD) to be implanted in a local chamber, comprising:
    electrodes provided on a housing of the LIMD;
    memory configured to store program instructions and a P-wave template;
    one or more processors that, when executing the program instructions, are configured to:
    utilizing the electrodes to obtain a far field (FF) cardiac activity (CA) signals for activity in a remote chamber of a heart;
    compare the far field CA signals to a P-wave template to identify a P-wave as an event of interest associated with the remote chamber, wherein the P-wave template is defined from an ensemble of FF CA signals, within a P-wave search window, for multiple beats;
    set an atrial-ventricular (AV) delay based on the P-wave identified; and
    deliver pacing pulses, utilizing the electrodes, at a pacing site of interest in the local chamber based on the AV delay.

11. The system of claim 10, wherein the one or more processors are further configured to form the P-wave template during an in-clinic feature set up that comprises:
    for multiple beats,
        obtaining surface ECG signals in parallel with calibration far field CA signals; and
        based on the ECG signals aligning a P-wave search window within the calibration far field CA signals; and
    combining segments of the calibration FF CA signals aligned with the P-wave search window for the corresponding multiple beats to form the P-wave template.

12. The system of claim 11, wherein the P-wave search window is defined, based on the ECG signals, manually or automatically.

13. The system of claim 11, wherein the one or more processors are further configured to: identify an R-wave in the calibration FF CA signals, automatically form the P-wave search window and align the P-wave search window with the calibration FF CA signals by a predetermined time interval prior to the R-wave in the calibration FF CA signals.

14. The system of claim 10, wherein the one or more processors are further configured to determine at least one of a correlation or root-mean-square relation of between the P-wave template and the FF CA signal.

15. The system of claim 10, wherein the LIMD is configured to be implanted in a right ventricle and the FF CA signals are indicative of cardiac events in the right atrium.

16. The system of claim 10, wherein the one or more processors are further configured to: obtain a collection of P-wave templates associated with at least one of different atrial activity sources or different patient postures; and compare two or more of the collection of P-wave templates to the FF CA signals to account for different morphologies of a candidate P-wave in the FF CA signal.

17. The system of claim 10, wherein the FF CA signals and P-wave template correspond to at least one an electrocardiogram (EGM) signal or a pressure signal.

18. The system of claim 10, wherein the one or more processors are further configured to: obtain repeated samples for the FF CA signal; and save the samples in a first-in-first-out buffer to maintain a series of the samples from the FF CA signals for a P-wave search window, the series of the samples compared to the P-wave template to identify the P-wave as the event of interest.

* * * * *